(12) United States Patent
Venkatesh et al.

(10) Patent No.: US 8,545,881 B2
(45) Date of Patent: Oct. 1, 2013

(54) ORALLY DISINTEGRATING TABLETS AND METHODS OF MANUFACTURE

(75) Inventors: Gopi M. Venkatesh, Vandalia, OH (US); Ken Kangyi Qian, Cincinnati, OH (US); Shyam Vangala, Huber Heights, OH (US); James M. Clevenger, Vandalia, OH (US); Donald Guenther, Brookville, OH (US)

(73) Assignee: Eurand Pharmaceuticals, Ltd., Dublin (IE)

( * ) Notice: Subject to any disclaimer, the term of this patent is extended or adjusted under 35 U.S.C. 154(b) by 1079 days.

(21) Appl. No.: 10/827,106

(22) Filed: Apr. 19, 2004

(65) Prior Publication Data

US 2005/0232988 A1    Oct. 20, 2005

(51) Int. Cl.
*A61K 9/20*    (2006.01)
*A61K 9/50*    (2006.01)

(52) U.S. Cl.
USPC ........... 424/464; 424/441; 424/465; 424/484; 424/489

(58) Field of Classification Search
USPC ................ 424/439, 440, 480, 459, 464, 470, 424/482, 494, 489, 490; 514/165, 419
See application file for complete search history.

(56) References Cited

U.S. PATENT DOCUMENTS

| | | | |
|---|---|---|---|
| 4,305,502 A | 12/1981 | Gregory et al. | |
| 4,371,516 A | 2/1983 | Gregory et al. | |
| 4,389,330 A | 6/1983 | Tice et al. | |
| 4,542,042 A | 9/1985 | Samejima et al. | |
| 4,661,647 A | 4/1987 | Serpelloni et al. | |
| 5,075,114 A | 12/1991 | Roche | |
| 5,082,669 A | 1/1992 | Shirai et al. | |
| 5,160,680 A | 11/1992 | Serpelloni et al. | |
| 5,178,878 A | 1/1993 | Wehling et al. | |
| 5,439,689 A | 8/1995 | Hendrickson et al. | |
| 5,464,632 A | 11/1995 | Cousin et al. | |
| 5,466,464 A * | 11/1995 | Masaki et al. | 424/434 |
| 5,576,014 A | 11/1996 | Mizumoto et al. | |
| 5,607,697 A * | 3/1997 | Alkire et al. | 424/495 |
| 5,700,492 A | 12/1997 | Morimoto et al. | |
| 5,720,974 A | 2/1998 | Makino et al. | |
| 5,738,875 A | 4/1998 | Yarwood et al. | |
| 5,876,759 A * | 3/1999 | Gowan, Jr. | 424/494 |
| 6,106,861 A | 8/2000 | Chauveau et al. | |
| 6,139,865 A | 10/2000 | Friend et al. | |
| 6,221,392 B1 | 4/2001 | Khankari et al. | |
| 6,269,615 B1 | 8/2001 | Amborn et al. | |
| 6,451,345 B1 * | 9/2002 | Percel et al. | 424/480 |
| 7,815,937 B2 * | 10/2010 | Mezaache et al. | 424/465 |
| 2001/0014340 A1 * | 8/2001 | Ohta et al. | 424/400 |
| 2002/0044962 A1 * | 4/2002 | Cherukuri et al. | 424/459 |
| 2002/0110597 A1 * | 8/2002 | Ryde et al. | 424/489 |
| 2003/0215500 A1 | 11/2003 | Ohta et al. | |
| 2004/0057993 A1 * | 3/2004 | Jain et al. | 424/465 |
| 2004/0068000 A1 * | 4/2004 | Guo et al. | 514/419 |
| 2005/0053655 A1 * | 3/2005 | Yang et al. | 424/464 |
| 2005/0152974 A1 | 7/2005 | Boehm et al. | |

FOREIGN PATENT DOCUMENTS

| | | |
|---|---|---|
| EP | 0052492 | 2/1984 |
| EP | 0538034 | 4/1993 |
| EP | 0553777 | 8/1993 |
| EP | 0721777 | 7/1996 |
| EP | 0 914818 A1 * | 6/1997 |
| EP | 0650826 | 6/1997 |
| EP | 0 914818 A1 * | 5/1999 |
| EP | 0914818 | 5/1999 |
| EP | 1156786 | 11/2001 |
| FR | 2679451 | 1/1993 |
| FR | 2766089 | 1/1999 |
| JP | 07-124231 | 5/1995 |
| WO | 93/12769 | 7/1993 |
| WO | 94/08576 | 4/1994 |
| WO | 97/41878 | 11/1997 |
| WO | 99/04763 | 2/1999 |
| WO | 00/51568 | 9/2000 |
| WO | 00/59486 | 10/2000 |
| WO | 02/057475 | 7/2002 |
| WO | 02/085336 | 10/2002 |
| WO | 03/013492 | 2/2003 |
| WO | 03/026613 | 4/2003 |

OTHER PUBLICATIONS

U.S. Appl. No. 60/615,501, filed Oct. 2004, Perrett.
U.S. Appl. No. 11/213,266, filed Aug. 26, 2005, Lai et al.

* cited by examiner

*Primary Examiner* — Michael G Hartley
*Assistant Examiner* — Jagadishwar Samala
(74) *Attorney, Agent, or Firm* — Cooley LLP

(57) ABSTRACT

A tablet that rapidly disintegrates in the oral cavity comprising a compressed blend of rapidly dispersing microgranules prepared by granulating a sugar alcohol or a saccharide or a mixture thereof having an average particle size less than about 30 microns and a disintegrant, and a taste-masked microcapsule containing at least one drug, the microcapsule being prepared by granulating a pharmaceutically acceptable formulation comprising at least one drug in a therapeutically effective amount and at least one polymeric binder that improves resilience of the microgranules, wet milling the granulated mass, and microencapsulating the milled granules to provide microcapsules.

21 Claims, No Drawings

ORALLY DISINTEGRATING TABLETS AND METHODS OF MANUFACTURE

FIELD OF THE INVENTION

The present invention relates to orally disintegrating tablets and a method for their manufacture. More particularly it relates to an orally disintegrating tablet made up of rapidly dispersing microgranules and taste-masked microcapsules.

Another embodiment of the invention relates to a tablet, which is compressed into a predetermined shape after blending the granulated material with a suitable lubricant. An ideal orally disintegrating tablet formulation rapidly disintegrates in the buccal cavity dispersing the contents and has a pleasant taste and smooth creamy mouthfeel (no grittiness), and complete drug release occurs in the gastrointestinal tract so as to be bioequivalent to the reference immediate release product. This convenience leads to better compliance with dosing regimen and as a consequence, to enhanced therapy. From an industrial/commercial utility point of view, the tablets should have sufficient strength to be suitable for packaging in HDPE bottles and push-through blisters for storage, transportation and distribution.

There are two types of most widely used dosage forms for oral administration: tablets and capsules. However, such dosage forms have several common disadvantages. For example, it may be hard for aged persons to swallow tablets or capsules or to medicate children who are unwilling to swallow tablets or capsules. It is also inconvenient for the 'people on the move' to take such dosage forms since they need to look for water. On the other hand, solid medicines, which rapidly dissolve or disintegrate in the buccal cavity, can be taken without water, so they may be easily taken by such aged persons, children or the 'people on the move'.

Different types of dosage forms disintegrating/dissolving rapidly in the buccal cavity have been developed and dosage forms comprising a number of actives are commercially available to enhance patient compliance. For instance, in JP-B-62-50445, solid dosage forms which can be produced from aqueous solutions containing gelatin and an active ingredient by freeze drying are disclosed. And in WO93/12769, solid medicines which can be produced by drying suspension including agar are also disclosed. However, the medicines produced by the above-mentioned prior methods do not have enough hardness for packaging in bottles or blisters for storage, transport and commercial distribution. Hence, they require special pharmaceutical techniques and hence, require huge investments in plants and equipment.

Three US patents (U.S. Pat. Nos. 4,305,502, 4,371,516, and 5,738,875) assigned to R. P. Scherer discloses Zydis technology based on freeze-drying, which is used to manufacture rapidly dissolving tablets. The potential drug should have a particle size<50 μm and should not have a bitter taste. Although the process is quite popular in the pharmaceutical industry, it is expensive and time-consuming. The products produced by this technology are fragile and require special packaging and handling. U.S. Pat. Nos. 5,178,878, 6,269,615 and 6,221,392, all assigned to Cima Labs, Inc., teach the art of manufacturing friable orally disintegrating tablets by direct compression and packaging in specially designed dome-shaped blister package using a robot-controlled integrated tableting-packaging system. U.S. Pat. Nos. 5,464,632 and 6,106,861 disclose methods of producing rapidly disintegrating multiparticulate tablets which disintegrate in the mouth within 60 seconds comprising an active in the form of microcrystals, coated microgranules or uncoated microgranules, 3 to 15% disintegrant, 40 to 90% of a soluble diluent which is a mixture of directly compressible polyols with an average particle size of 100 to 500μ and powdered polyols with an average particle size of less than 100μ.

Takeda Chemical Industries (EP 0,553,777 A2 and U.S. Pat. No. 5,720,974) disclose production methods wherein tablets composed of a saccharide are produced in such a manner that a saccharide mixture supplied with appropriate water is compressed at a low pressure and then dried to make solid tablets. However, such methods also require a special pharmaceutical technique and have the fear that powder composing the tablets may be adhered to the surface of a metal mold in compression process under moistening condition. It may be therefore difficult to utilize those methods in manufacturing use in a plant. Furthermore, such dosage forms require well taste masked drug particles.

Mizumoto et al. (U.S. Pat. No. 5,576,014) have classified sugar-based excipients into two types on the basis of their moldability and dissolution rate. The moldability of a low molding sugar such as mannitol is improved by granulating with a high molding excipient and this is the basis of WOWTAB technology. Ethypharma has introduced an orally dispersible Flash Dose technology, which contains coated crystals and microgranules along with disintegrants, a soluble diluent, a lubricant and optionally a swelling agent (EP 1156786 and WO 2002085336 A1).

US Patent Application No. 200100114340 published on Aug. 16, 2001 and EP Application No. EP 0 914818 A1 published on Dec. 5, 1999, disclose a simple method for manufacturing tablets rapidly disintegrating/dissolving in the buccal cavity by granulating widely used excipients (a sugar alcohol or saccharide such as mannitol or lactose, a disintegrant such as crospovidone) optionally with an active to produce soft dispersible microgranules, blending with other excipients and compressing into rapidly disintegrating tablets using conventional granulating, drying and tableting equipment. These and additional embodiments are disclosed in U.S. patent application Ser. No. 10/356,641. A group of patents (JP 2681601, U.S. Pat. No. 5,700,492, EP 650826) disclose a method of manufacturing tablets disintegrating in the buccal cavity in less than 60 seconds, the tablet being further characterized in that it is formed by compressing in a tableting machine using a punch and a die that have been previously coated with a lubricant, the tablet formulation otherwise being free of lubricant. Eurand has licensed both these technologies from Kyowa Hakko Kogyo Company in Japan and are incorporated in their entirety by reference. The compression blends to be tableted are typically pre-blended with lubricants such as magnesium stearate and stearic acid which being highly hydrophobic retard water penetration into the tablet and hence may delay its disintegration/dissolution especially in the buccal cavity. The use of externally lubricated punches and dies and rapidly dispersing microgranules disclosed in these patents and patent applications significantly improve the disintegration properties of tablets containing high doses of taste-masked actives with a bitter taste. Furthermore, these tablets are suitable for packaging in HDPE bottles and in blister packs using conventional equipment for storage, transportation and commercial distribution.

Many of the active pharmaceutical ingredients are bitter in taste and require effective taste-masking before they can be incorporated into tablets which rapidly disintegrate/disperse in the buccal cavity. Another requirement for being incorporated into rapidly disintegrating tablets is that the taste-masked microcapsules/granules should be smaller than 500 μm in diameter, preferably be smaller than 400 μm in diameter to avoid gritty mouthfeel.

U.S. Pat. No. 5,075,114 assigned to Roche, U.S. Pat. No. 5,082,669 assigned to Shirai et al., U.S. Pat. No. 4,389,330 to Tice et al., and U.S. Pat. Nos. 4,389,331 and 4,542,042 assigned to Samejima et al. disclose methods of taste-masking using a variety of techniques. However, these methods have several limitations including forming large agglomerations and improper coating (and hence poor taste-masking).

WO 94/08576 with a priority date of 16 Oct., 1992 discloses a composition which is substantially free of the bitter taste of ranitidine HCl and comprises particles comprising ranitidine HCl incorporated into a core and coated with a lipid coating, wherein the poorly water soluble core is prepared by dispersing ranitidine HCl in an ethylcellulose solution in methylene chloride or in molten carnauba wax and the lipid is typically a mixture of mono-, di- or triester or glycerol. The tablet comprising the taste-masked ranitidine has an unacceptable drug load of 5-10% w/w.

U.S. Pat. No. 6,139,865 assigned to Eurand discloses a method of taste-masking a bitter drug such as ranitidine hydrochloride by coacervation in a cyclohexane solution containing ethylcellulose and polyethylene as a phase inducer. The microcapsules thus produced are successfully incorporated in effervescent tablet formulations exhibiting acceptable taste-masking, aftertaste, and overall acceptance characteristics. For use in an orally disintegrating tablet, the particle size of most of the taste-masked microcapsules should be less than 400 μm or less to avoid gritty mouthfeel. This translates into a desired particle size distribution for the active in the range of 75-200 μm. It is often difficult if not impossible in some cases to produce active drug particles with narrow size distributions. Often, the actives contain fines (under sized particles) as well as over sized particles. In order to better control the particle shape and size distribution of the active pharmaceutical ingredient, the active is milled or micronized. It is a challenge to taste mask such fine powders. The ordinary wet granulation methods using a widely used binder such as Povidone (polyvinylpyrrolidone) produce fragile/friable granules, which break down or fracture due to rapid agitation during microencapsulation by coacervation. The use of widely used binders at high concentrations results in large oversized granules, which produce fines during dry milling, and hence are not suitable for taste masking by coacervation. The present invention provides a method for the manufacture of resilient microgranules with most desired particle size distributions, which are suitable for effectively taste-masking by coacervation in accordance with methods disclosed in U.S. Pat. No. 6,139,865, which is incorporated in its entirety by reference. The present invention also provides a method for manufacturing tablets, which rapidly disintegrate in the buccal cavity. U.S. Pat. No. 5,700,492 and EP 650826 and US Patent Application No. 20010014340 published on Aug. 16, 2001 and EP Application No. EP 0 914818 A1 published on Dec. 5, 1999, which were licensed to Eurand were incorporated in their entirety by reference.

SUMMARY OF THE INVENTION

Microgranules suitable for microencapsulation by coacervation should have sufficient strength and sufficiently low friability to withstand attrition caused by agitation during microencapsulation. At the same time, these microcapsules following microencapsulation should be capable of being compacted into tablets with minimal membrane fracture as membrane fracture results in undesired drug release causing bitter taste.

One embodiment of this invention relates to pharmaceutical compositions comprising rapidly dispersing microgranules of a disintegrant and sugar alcohol or a saccharide whose average particle size is not more than 30 μm, resilient (hard, flexible, less-friable) microgranules of bitter active pharmaceutical ingredients effectively taste-masked by coacervation, and other pharmaceutically acceptable excipients in the form of tablets which rapidly disintegrate in the buccal cavity. Another embodiment of the invention additionally provides a method of manufacturing rapidly disintegrating microgranules of a sugar alcohol or a saccharide in combination with a disintegrant, resilient microgranules taste-masked by coacervation, and compressing these two granules along with other excipients such as color, flavor, sweetener into tablets, the tablet thus produced having the property that it is formed by compressing in a tablet press equipped with an externally lubricating system to pre-lubricate dies and punches and the tablet formulation otherwise being free of lubricant.

In accordance with the one embodiment of the invention, milled/micronized drug particles (e.g., average particle diameter less than about 50 μm, preferably less than about 25 μm) are blended with a water soluble ductile polymeric binder such as modified starch and hydroxypropyl methylcellulose with a viscosity of 100 cps or higher, alone or in combination with a widely used binder such as PVP (polyvinylpyrrolidone), hydroxypropylcellulose and hydroxypropyl methylcellulose with a viscosity of 15 cps or less. This wet mass is milled using a size reduction mill (for example: Comil™ run at a slow speed) equipped with a suitable size sieve in order to produce resilient (hard, flexible, less-friable) particles thereby avoiding excessive dry milling which produce fines. These granules can be obtained with an average particle size of 200 μm and can be effectively taste masked by coacervation by phase separation to produce taste-masked particles with optimum size distribution (e.g., mean particle size of not more than 400 μm) for incorporation into tablets, which rapidly disintegrate in the buccal cavity with a smooth creamy mouthfeel.

It is still another embodiment of the invention to provide a method of blending taste-masked microcapsules with rapidly dispersing microgranules produced by granulating, without a conventional binder, a sugar alcohol or a saccharide or a mixture thereof, with an average particle size of not more than 30 μm and a disintegrant, and other pharmaceutically acceptable excipients and compressing the blend into tablets which rapidly disintegrate (e.g., less than 120 seconds, preferably less than 60 seconds) in the buccal cavity.

It is yet another embodiment of the invention to provide a method to manufacture rapidly disintegrating tablets, which are characterized by the property that it is formed by compressing in a tablet press equipped with an externally lubricating system to pre-lubricate dies and punches and the tablet formulation otherwise being free of lubricant. Intrabuccally rapidly disintegrating tablets exhibit sufficient hardness and sufficiently low friability and are suitable for packaging in HDPE bottles and blister packs using conventional equipment for storage, transportation and commercial distribution.

DETAILED DESCRIPTION OF THE INVENTION

From pharmaceutical and practical points of view, the inventors have examined various methods of taste-masking before coming up with a method which has wider applicability and also evaluated methods of producing intrabuccally rapidly disintegrating tablets, which don't require a special pharmaceutical production technique and can be simply and easily produced by a normal equipment. As a result, the inventors have developed, as a convenient method for effectively taste-masking bitter drug particles producing microcapsules of most desired particle size distributions, which are suitable for incorporation into tablets having the property of rapidly disintegrating in the buccal cavity and leaving no aftertaste (good creamy mouthfeel instead). The invention also provides a method of manufacturing pharmaceutical tablets, produced by mixing microgranules of a sugar alcohol such as D-mannitol or a saccharide such as lactose, each having an average particle diameter of not more than 30 μm, preferably not more than 20 μm and a disintegrant with one or more taste-masked microcapsules and other excipients (for example: flavor, color, sweetener etc.) and compressing the blend into rapidly disintegrating tablets, the tablet thus produced having the property that it is formed by compressing in a tablet press equipped with an externally lubricating system to pre-lubricate dies and punches and the tablet formulation otherwise being free of lubricant.

A method of manufacturing tablets in accordance with one embodiment of the invention, which rapidly disintegrate in the buccal cavity without leaving undesirable mouth feel comprises the following steps:

(a) granulating a sugar alcohol or a saccharide, or a combination thereof, each of which has an average particle diameter of not more than 30 μm with a disintegrant such as Crospovidone using water or an alcohol-water mixture at a ratio of 1:3 to 3:1, without the addition of a binder, in a typical high shear granulator, wet milling to produce a desired particle size distribution, and drying in a fluid bed equipment to produce dispersible microgranules with an average particle size of not more than 400 μm (typically the average particle size of not more than 300 μm);

(b) granulating a bitter active pharmaceutical ingredient and optionally one or more pharmaceutically acceptable diluents such as mannitol, lactose and microcrystalline cellulose with at least one polymeric binder such as modified starch and hydroxypropylmethylcellulose with a viscosity of 100 cps or higher, which imparts resilient, characteristics to the dried granules and wet milling using a size reduction mill such as Comil™ equipped with an appropriate sieve size to produce granules with a desired particle size distribution in order to avoid excessive dry milling which typically results in fines undesirable from the taste-masking point of view;

(c) microencapsulating these resilient granules (mean size: 200 μm or less) by coacervation in cyclohexane containing ethylcellulose to produce effectively taste-masked microcapsules with a desired particle size distribution (average particle size of not more than 400 μm, typically not more than 300 μm) wherein the average membrane thickness is in the range of 30% to 50% by weight of the coated granules;

(d) blending dispersible microgranules of step (a) with taste-masked microcapsules of step (c), and other acceptable ingredients such as a flavoring agent, a coloring agent, a sweetener and additional disintegrant in sufficient quantities to provide a therapeutically effective unit dose; and (e) compressing into tablets using a conventional rotary tablet press equipped with an external lubrication system to pre-lubricate the dies and punches, wherein the ratio of effectively taste-masked microgranules to dispersible microgranules is in the range of 1:1 to 1:10, preferably 1:2 to 1:5 approximately.

The term 'drug', 'active' or 'active pharmaceutical ingredient' as used herein is meant to include any therapeutic active agent indicated for oral administration such as macrolide antibiotic agents, analgesics, antidepressants, antihistamines, antihypertensives, antimigrane agents, proton pump inhibitors, antipsychotic agents, antiemetic agents, antiparkinson agents, and $H_2$ antagonists. In one embodiment, the drug candidates include ranitidine, cimetidine, clarithromycin, sumatriptan, lansoprazole, caffeine, cetirizine and their salts thereof. The active, in one embodiment has a particle size less than about 50 microns and is present in the tablet in an amount of about 0.01 to 30% by weight. In one embodiment the active has a particle size less than about 25 microns.

Polymers which impart resilient characteristics to the dried microgranules, include hydroxypropylcellulose (Klucel LF from Aqualon) modified starch (e.g., Starch 1551 and Starch 1500, commercially available from National Starch and Colorcon, respectively) and hydroxypropyl methylcellulose with a viscosity of 100 cps or more (e.g., Methocel K100LV or Metolose K400 commercially available from Dow Chemical and Shin Etsu Chemicals, respectively) alone or in combination with a widely used binder such as PVP (polyvinylpyrrolidone), hydroxypropylcellulose and hydroxypropyl methylcellulose with a viscosity of 15 cps or less (Methocel E5 or E15 and Pharmacoat 603 or 606 commercially available from Dow Chemical and Shin Etsu Chemicals, respectively).

Polymers suitable for microencapsulation of bitter drugs include ethylcellulose, cellulose acetate phthalate, hydroxypropyl methylcellulose phthalate depending on solubility in water or cyclohexane. No plasticizer is needed for forming membranes on active cores for effective taste-masking. One method for microencapsulating microgranules of the active to impart effective taste-masking characteristics is coacervation by phase separation of ethylcellulose in cyclohexane. Examples of such a coacervation process are disclosed in U.S. Pat. No. 6,139,865, which is incorporated in its entirety by reference.

One or more sugar alcohols and/or saccharides with an average particle size of not more than 30 μm and a disintegrant are granulated with approximately 20-25% water in a high shear granulator, wet milled, dried in a fluid bed equipment to produce rapidly dispersible microgranules of desired particle size (average particle size of not more than about 300 μm in accordance with methods disclosed in USP Application No. 200100114340 published on Aug. 16, 2001). The sugar alcohol may be selected from the group consisting of mannitol, sorbitol, xylitol, maltitol and the like while the saccharide may be selected from the group consisting of lactose, sucrose, maltose or as a mixture of two or more, each of which is characterized by an average particle size of not more than about 30 μm. In one embodiment the sugar alcohol and/or saccharide is present in the tablet in an amount of about 30 to 70% by weight.

A disintegrant is selected from the group consisting of crospovidone (crosslinked PVP), sodium starch glycolate, crosslinked sodium carboxymethyl cellulose, calcium silicate and low substituted hydroxypropyl cellulose. The disintegrant is typically present in the tablet in an amount of about 1 to 10% by weight. The disintegrant has a particle size less than about 30 microns in one embodiment.

In addition to coated microgranules of the active(s) in appropriate quantities, dispersible microgranules, and additional disintegrant as needed, the tablet produced in accordance with the embodiments of the present invention may contain suitable flavors, sweeteners, permissible colorants as needed. A lubricating agent such as magnesium stearate is not typically blended with this compression mix; but the punches and dies are pre-lubricated with a fine mist of of the lubricant using an external lubrication system. Thus the hydrophobic lubricant is only present in trace quantities and that too on the tablet surface. This act of external lubrication permits rapid penetration of the saliva in the mouth into the tablet core resulting in rapid disintegration/dispersion of the tablet into granules. These granules soaked in the saliva are carried down the throat into the stomach where the drug is released for maximum efficacy. The act of blending the lubricant with the compression mix and tableting using a conventional tablet press is also an embodiment of the present invention.

It is to be understood that while the invention has been described in conjunction with the preferred specific embodiments thereof, that the description above as well as the examples which follow below are intended to illustrate and not limit the scope of the invention. Any modification within the scope of the invention will be apparent to those skilled in the art to which the invention pertains.

Example 1

Comparison

Dispersible Microgranules:

The dispersible microgranules comprise a sugar alcohol such as mannitol and a disintegrant. 6.65 kg of mannitol with an average particle size of approximately 10 μm (Pearlitol 25 from Roquette, France) was blended with 350 g of crosslinked povidone (Crospovidone XL 10 from ISP) in a high shear granulator (GMX 25 from Vector) and granulated with sufficient amount of purified water (approximately 1.6 kg) and wet milled using Comil (from Quadro) and dried in a fluid bed drier, Glatt GPCG 5. The dispersible microgranules thus obtained has an average particle size of approximately 160 μm.

Ranitidine Granulation:

400 g of ranitidine HCl was blended with 360 g of mannitol with an average particle size of not more than 25 μm, 40 g of low viscosity hydroxypropyl methylcellulose (Methocel E5) and granulated with purified water. The wet mass was milled using a Comil and dried in the oven at 40° C. for 3 hours.

Microencapsulation:

The granules thus obtained were suspended in a solution of cyclohexane containing ethylcellulose with a viscosity of approximately 100 cps and polyethylene at approximately 80° C. and membrane coated by properly cooling (coacervation). The microencapsulated granules were washed and dried. The granules (friable with 40% fines when tested by the friability test procedure) were found to undergo attrition due to agitation in the coacervation tank. The microcapsules thus obtained exhibited poor taste masking.

Example 2

Ranitidine Granulation:

400 g of ranitidine HCl was blended with 360 g of mannitol with an average particle size not more than 25 μm, 40 g of hydroxypropyl methylcellulose with an average viscosity of 400 cps and granulated with an aqueous solution of low viscosity hydroxypropyl methylcellulose (Methocel E5). The wet mass was milled using a Comil and dried in the oven at 40° C. for 3 hours. The granules thus obtained were rigid/less friable with a desired particle size distribution (range: most particles in the range of 140-300 μm).

Microencapsulation:

These granules were taste-masked by coacervation following the procedure given in Example 1. The microcapsules thus obtained contained largely intact granules and exhibited improved taste masking. The Laser light scattering and palatability testing suggests that the microcapsules with most desired particle size distribution (average particle size: 368 μm) exhibits an improved taste-masking.

Tableting:

Dispersible microgranules (59.5%) were blended with taste-masked microcapsules (30.5%) and other pharmaceutical acceptable ingredients, such as flavor, sweetener, colorant, and additional disintegrant in sufficient quantity to provide a therapeutically effective unit dose (75 mg ranitidine), in a twin shell V-blender for a sufficient time to get homogeneously distributed blending for compression. Unit dose was measured on an analytical balance and compressed into tablet (weighing approximately one gram with a disintegration time of 45-60 seconds) at an optimized compression force on a carver press.

Dissolution Testing:

Both microcapsules and tablets were tested for dissolution using USP Apparatus 2 (paddles@ 50 rpm) in 900 mL medium at 37° C. and percentage of drug released was determined by HPLC. The results are presented in the table below:

| | Drug released % | |
|---|---|---|
| Time | Microcaps (966-DLG-183) | Tablet (984-VS-133-D) |
| 5 min | 8 | 67 |
| 10 min | 24 | 85 |
| 20 min | 48 | 92 |
| 30 min | 60 | 97 |
| 45 min | 70 | 100 |
| 60 min | 77 | 100 |
| 120 min | 87 | 100 |

Example 3

Granulation:

651 g of ranitidine HCl was blended with 49 g of hydroxypropyl methylcellulose with an average viscosity of 400 cps and granulated with purified water. The wet mass was milled using a Comil and dried in the oven at 40° C. for 3 hours. The granules thus obtained were rigid/less friable with a desired particle size distribution (range: most particles in the range of 200-400 μm).

Microencapsulation:

These granules were taste-masked by coacervation following the procedure given in Example 1. The microcapsules thus obtained contained largely intact granules and exhibited improved taste masking. The Laser light scattering and palatability testing suggests that the microcapsules with most desired particle size distribution (average particle size: 400 μm) exhibits an improved taste-masking.

Tableting:

Dispersible microgranules (73.9%) were blended with taste-masked microcapsules (16.1%) and other pharmaceutical acceptable ingredients, such as flavor, sweetener, colorant, and additional disintegrant in sufficient quantity to provide a therapeutically effective unit does, in a twin shell V-blender for a sufficient time to get homogeneously distributed blending for compression. Unit dose (approximately 1 g) was measured on an analytical balance and compressed into tablet at an optimized compression force on a carver press.

Dissolution Testing:

Microcapsules and tablets were tested for dissolution using USP Apparatus 2 (paddles@ 50 rpm) in 900 ml medium at 37° C. and percentage of drug released was determined by HPLC. The results are presented in the table below:

| | Drug Released % | |
|---|---|---|
| Time | Microcaps (1008-KKQ-094-B-1) | Tablet (984-VS-133-C) |
| 5 min | 11 | 43 |
| 10 min | 27 | 63 |
| 20 min | 47 | 77 |
| 30 min | 57 | 84 |
| 45 min | 68 | 88 |
| 60 min | 74 | 90 |
| 120 min | 89 | 94 |

Example 4

Granulation:

600 g of ranitidine HCl was blended with 66.7 g of modified starch, Starch 1500 from Colorcon and granulated with purified water. The wet mass was milled using a Comil and dried in the oven at 40° C. for 3 hours. The granules thus obtained were rigid/less friable with a desired particle size distribution (range: most particles in the range of 140-300 µm).

Microencapsulation:

These granules were suspended in cyclohexane containing ethylcellulose with a viscosity of approximately 100 cps and polyethylene at approximately 80° C. and membrane coated by properly cooling (coacervation). The microencapsulated granules were washed and dried. The microcapsules thus obtained contained largely intact granules and exhibited excellent taste-masking.

Tableting:

Dispersible microgranules (68.9%) were blended with taste-masked microcapsules (20.1%) and other pharmaceutical acceptable ingredients, such as flavor, sweetener, colorant, and additional disintegrant in sufficient quantity to provide a therapeutically effective unit does, in a twin shell V-blender for a sufficient time to get homogeneously distributed blending for compression. Unit dose weighing approximately one gram was measured on an analytical balance and compressed into tablet at an optimized compression force on a carver press.

Dissolution Testing:

Both microcapsules and tablets were tested for dissolution using USP Apparatus 2 (paddles@ 50 rpm) in 900 mL medium at 37° C. and percentage of drug released was determined by HPLC. The results are presented in the table below:

| | Drug Released % | |
|---|---|---|
| Time | Microcaps (1029-DLG-006) | Tablet (1008-KKQ-134-C-AdvaTab) |
| 5 min | 12 | 42 |
| 10 min | 27 | 63 |
| 20 min | 45 | 80 |
| 30 min | 54 | 86 |
| 45 min | 63 | 91 |
| 60 min | 68 | 93 |
| 120 min | 80 | 96 |

Example 5

Dispersible Microgranules:

The dispersible microgranules comprise a sugar alcohol such as mannitol and a disintegrant. 152 kg of mannitol with an average particle size of approximately 10 µm (Pearlitol 25 from Roquette, France) was blended with 8 kg of crosslinked povidone (Crospovidone XL 10 from ISP) in a high shear granulator (GMX 600 from Vector) and granulated with sufficient amount of purified water (approximately 32 kg) and wet milled using Comil (from Quadro) and dried in a fluid bed drier, Glatt GPCG 200. The dispersible microgranules thus obtained has an average particle size of approximately 160 µm.

Granulation:

5.0 kg of ranitidine HCl was blended with 600 g of modified starch, Starch 1500 from Colorcon and granulated with purified water in high shear mixer GMX 25 (from Vector). The wet mass was milled using a Comil and dried in the oven at 40° C. for 3 hours. The granules thus obtained were hard/non-brittle with a desired particle size distribution (average particle size: 150 µm).

Microencapsulation:

These granules were suspended in cyclohexane containing ethylcellulose with a viscosity of approximately 100 cps and polyethylene at approximately 80° C. and membrane coated by properly cooling (coacervation). The microencapsulated granules were washed and dried. The microcapsules thus obtained contained largely intact granules with an average particle size of 150 µm and exhibited excellent taste-masking.

Tableting:

Dispersible microgranules (5.4 kg) were blended with taste-masked microcapsules (1.06 kg from lots (1029-DLG-16 and 1029-DLG-17)) and other pharmaceutical acceptable ingredients, such as flavor, sweetener, colorant, and additional disintegrant in sufficient quantity to provide a therapeutically effective unit does, in a twin shell V-blender for a sufficient time to get homogeneously distributed blending for compression. Tablets weighing approximately 1 g were compressed using a production scale Hata Tablet press equipped with Matsui external lubrication system at an average hardness of 5.5 and 6.9 kP, respectively.

Dissolution Testing:

Microcapsules and tablets were tested for dissolution using USP Apparatus 2 (paddles@ 50 rpm) in 900 mL medium at 37° C. and percentage of drug released was determined by HPLC. The results are presented in the table below:

| | Drug Released % | | |
|---|---|---|---|
| | Microcaps | | Tablets 984-VS-152-2 |
| Time | 1029-DLG-016 | 1029-DLG-017 | (Hardness: 7.8 kP) |
| 5 min | 8 | 4 | 27 |
| 10 min | 23 | 15 | 47 |
| 20 min | 42 | 33 | 65 |
| 30 min | 52 | 44 | 75 |
| 45 min | 63 | 53 | 80 |
| 60 min | 70 | 62 | 82 |
| 120 min | 81 | 75 | 90 |

Example 6

Compressible Microcaps:

The microcapsules obtained in Example 4 were provided with a compressible coating of an aqueous dispersion of ethylcellulose (a fracture resistant, compressibility enhancing coating at 4% weight gain) in the fluid bed equipment. The coated microcaps were dried and cured. The microcapsules thus obtained exhibited excellent taste-masking. The dissolution was not affected.

Tableting:

Dispersible microgranules were blended with taste-masked microcapsules and other pharmaceutical acceptable ingredients, such as flavor, sweetener, colorant, and additional disintegrant in sufficient quantity to provide a therapeutically effective unit does, in a twin shell V-blender for a sufficient time to get homogeneously distributed blending for compression. Unit dose was measured on an analytical balance and compressed into tablet at an optimized compression force on a carver press.

Dissolution Testing:

Microcapsules and tablets were tested for dissolution using USP Apparatus 2 (paddles@ 50 rpm) in 900 mL medium at 37° C. and percentage of drug released was determined by HPLC. The results are presented in the table below:

| | Drug Released % | |
|---|---|---|
| Time | Microcaps (1029-DLG-015/ 904-MDS-151) | Tablets |
| 5 min | 7 | 24 |
| 10 min | 21 | 45 |
| 20 min | 39 | 63 |
| 30 min | 50 | 74 |
| 45 min | 58 | 85 |
| 60 min | 66 | 88 |
| 120 min | 80 | 98 |

Example 7

Granulation:

500 g of sumatriptan succinate was blended with 56 g of hydroxypropyl methylcellulose, HPMC K100LV, Hypromellose K100LV from Dow Chemical and granulated with purified water. The wet mass was milled using a Comil and dried in the oven at 40° C. for 3 hours. The granules thus obtained were rigid/less friable with a desired particle size distribution (range: most particles in the range of 200-360 μm).

Microencapsulation:

These granules were suspended in cyclohexane containing ethylcellulose with a viscosity of approximately 100 cps and polyethylene at approximately 80° C. and membrane coated by coacervation at two coating levels (lot#1029-DLG-018 at 45% coating and lot#1029-DLG-024 at 35% coating). The microencapsulated granules were washed and dried. The microcapsules thus obtained contained largely intact granules and exhibited excellent taste-masking.

Tableting:

Dispersible microgranules of both microcapsule batches were blended with taste-masked microcapsules and other pharmaceutical acceptable ingredients, such as flavor, sweetener, colorant, and additional disintegrant in sufficient quantity to provide a therapeutically effective unit does, in a twin shell V-blender for a sufficient time to get homogeneously distributed blending for compression. Unit dose was measured on an analytical balance and compressed into tablet at similar compression force on a carver press (100 mg (as sumatriptan base) tablets weighing 1200 mg, hardness: 8-9 kP and disintegration time: approximately 30 seconds).

Dissolution Testing:

Microcapsules were tested for dissolution using USP Apparatus 2 (paddles@ 50 rpm) in 900 ml medium (0.1N HCl with 0.1% sodium lauryl sulfate) at 37° C. and percentage of drug released was determined by HPLC. The results are presented in the table below:

| | Drug Released % | | | |
|---|---|---|---|---|
| Time | Microcaps (1029-DLG-018) 45% Coating | Tablet (1034-KKQ-009-C-T) 45% Coating | Microcaps (1029-DLG-024) 35% Coating | Tablet (1029-DLG-024-T) 35% Coating |
| 5 min | — | 3 | 1 | 8 |
| 15 min | 3 | 9 | 7 | 21 |
| 30 min | 14 | 25 | 30 | 47 |
| 45 min | 37 | 50 | 62 | 72 |
| 60 min | 64 | 75 | 84 | 89 |
| 90 min | 94 | 102 | 99 | 102 |
| 120 min | 102 | 109 | 102 | 104 |

Friability Testing:

The table presents the friability data for Ranitidine HCl and Sumatriptan succinate microgranules of examples 1 to 5 and 7.

| Friability | | |
|---|---|---|
| Example | Granulation batch | Friability (% fines generated) |
| No 1 | 1008-KKQ-025-A | 40 |
| No 2 | 1008-KKQ-027-K | 12 |
| No 3 | 1008-KKQ-094-B | 9 |
| No 4 | 1008-KKQ-134-C | 10 |
| No 5 | 1008-KKQ-140-B-1 | 8 |
| No 7 | 1034-KKQ-009-C | 9 |

Fine powders of pharmaceuticals, ores, foods, ceramics, and other materials are often agglomerated in various industrial processes and used as granules to overcome difficulties in handling or processing. These agglomerates or granules are required to have various properties, depending on the end use. Above all, granules must have the property of maintaining their integrity during handling and processing. Granules must flow for easy handling and transportation, and that means granules must have proper shape and particle size distribution. Furthermore, granules must be strong enough to maintain their integrity, e.g. shape/size, i.e., should not break or attrition or should exhibit sufficient strength and sufficiently low friability to withstand attrition during handling or processing, such as microencapsulation. At the same time, the microcapsules produced from these granules must be capable of being compacted into tablets with minimal membrane fracture; otherwise, tablets may exhibit undesirable aftertaste.

Granule size can be evaluated using a set of sieves or using a laser light scattering instrument. However, there are no well-established methods or instrumental techniques for rapid/easy testing of granule strength. An in-house method for evaluation of friability of granules to be used for microencapsulation has been developed and described below. This is a measure of the friability or integrity of the granules under dynamic or usage conditions.

The new test method uses a sieve shaker, an apparatus for the measurement of particle size distribution, with a test sieve (typically 140 mesh screen with an opening of approximately 105 μm or as appropriate depending on the particle size distribution of granules), a pan and grinding balls. During the testing, fines produced if the test sample is friable, pass through the sieve and are collected in the pan. Typically 20 grams granules and 100 g of 7-mm diameter ceramic grind balls are placed on the sieve and are subjected to shaking at medium setting for 10 min. At the end of the test, the ceramic balls are separated, the sieve containing the test sample is weighed and % friability is calculated. Based on several measurements and visual and microscopic observations on the microcapsules producing using granules subjected to friability testing, a friability value of 15% is considered an upper limit for granules to be suitable for microencapsulation.

Changes may be made by persons skilled in the art in the construction and the various components and assembly described herein or in the steps or the sequence of steps of the method of manufacture described therein without departing from the spirit and scope of the invention as defined in the following claims:

What is claimed:

1. A tablet that rapidly disintegrates in the oral cavity comprising a compressed blend of:
    rapidly dispersing microgranules comprising a sugar alcohol or a saccharide or a mixture thereof having an average particle size not more than about 30 microns, and a disintegrant, and
    taste-masked microcapsules containing at least one drug, prepared by granulating a pharmaceutically acceptable formulation comprising the at least one drug in a therapeutically effective amount and at least one polymeric binder imparting resilient characteristics to the resulting microcapsules, wet milling the granulated mass to form milled granules, and coating the milled granules with one or more polymers to provide taste-masked microcapsules, wherein the polymeric binder imparting resilient characteristics is selected from the group consisting of hydroxypropylcelluose (HPC) of viscosity of 100 cps or higher, hydroxypropyl methylcelluose (HPMC) with a viscosity of 100 cps or more, modified starches, and combination thereof,
    wherein not less than 60% of the at least one drug from said tablet dissolves in about 60 minutes when dissolution tested using USP Apparatus 2 (paddle at 50 RPM, 900 mL of 0.1N HCl at 37° C.).

2. The tablet of claim 1 prepared by a process comprising the steps of:
    (a) granulating the pharmaceutically acceptable formulation comprising at least one drug in a therapeutically effective amount and at least one polymeric binder imparting resilient characteristics to the resulting microcapsules, and optionally a diluent(s) and a disintegrant, and
    (b) wet milling the granulated mass using a size reduction mill to produce microgranules which resist breakage during coating for taste-masking and whose average particle size is not more than about 300 μm,
    (c) microencapsulating the microgranules to provide microcapsules with an average particle size of not more than about 400 μm,
    (d) separately granulating a sugar alcohol or a saccharide or a mixture thereof having an average particle size less than about 30 μm and a disintegrant to provide rapidly dispersing microgranules,
    (e) blending the taste-masked microcapsules from step (c) and rapidly dispersing microgranules from step (d) optionally with additional pharmaceutical ingredients,
    (f) compressing the blend from step (e) to form a tablet.

3. The tablet of claim 1 which is produced by:
    (a) granulating a powder mixture into rapidly dispersing microgranules with a fixed particle diameter, the powder mixture comprising a sugar alcohol, a saccharide or a combination thereof, each of which having an average particle diameter of not more than 30 μm;
    (b) granulating, wet milling and drying a pharmaceutically acceptable formulation comprising at least one drug with an average particle size of not more than about 50 μm, at least one polymeric binder imparting resilient characteristics to the resulting microcapsules, and optionally a diluent(s) and a disintegrant, said microgranule exhibiting not more than 15% fines (passing through 140 mesh screen) when tested in accordance with the procedure for friability test;
    (c) encapsulating the microgranules of the at least one drug of step (b) by coacervation in a cyclohexane solution comprising ethylcellulose,
    (d) mixing the rapidly dispersing microgranules from step (a) and the microcapsules from step (c) and optionally other pharmaceutically acceptable ingredients and compressing the mixture into a predetermined shape.

4. The tablet as set forth in claim 1 comprising rapidly dispersing microgranules comprising a sugar alcohol, a saccharide or a combination thereof, each of which has an average particle size of not more than about 30 μm, in the amount of about 30-70% by weight of the tablet; a taste-masked microcapsule having an average particle diameter of not more than about 400 μm in the amount of about 0.01-30% by weight of the tablet; a disintegrant in the amount of about 1.0-10% by weight of the tablet, and optionally other pharmaceutically acceptable ingredients, said tablet being compressed into a predetermined shape.

5. The tablet of claim 4 wherein said sugar alcohol or saccharide is selected from the group consisting of D-mannitol, sorbitol, xylitol, maltitol, lactose and combinations thereof; and wherein the disintegrant is selected from the group consisting of crospovidone, sodium starch glycolate, crosslinked carboxymethyl cellulose, and low substituted hydroxypropyl cellulose and combinations thereof, each of which have an average particle diameter of not more than about 30 μm.

6. The tablet as set forth in claim 5 wherein the sugar alcohol is D-mannitol.

7. The tablet as set forth in claim 5 wherein the saccharide is lactose.

8. The tablet of claim 4 wherein said at least one drug is selected from the group consisting of $H_2$ antagonists, proton pump inhibitors, $H_5$ agonists, and selective histamine $H_1$ receptor antagonists, each of which having an average particle size of not more than about 50 μm.

9. The tablet of claim 8 wherein the disintegrant is selected from the group consisting of cross-linked polyvinylpyrrolidone (crospovidone), cross-linked carmellose of sodium, low substituted hydroxypropylcellulose and mixtures thereof.

10. The tablet as set forth in claim 8 wherein the at least one drug is selected from the group consisting of ranitidine, cimetidine, famotidine, omeprazole, lansoprazole, sumatriptan, rezatriptan, zolmitriptan and cetirizine.

11. The tablet as set forth in claim 10 wherein the at least one drug is sumatriptan.

12. The tablet as set forth in claim 11 wherein the disintegrant is crospovidone.

13. The tablet as set forth in claim 1 wherein the disintegration time in the buccal cavity of the tablet is not more than 120 seconds.

14. A method for manufacturing a tablet of claim 1 that rapidly disintegrates in the oral cavity comprising the steps of:
- (a) granulating a pharmaceutically acceptable formulation comprising at least one drug in a therapeutically effective amount and at least one polymeric binder imparting resilient characteristics to the resulting microcapsules, and optionally a diluent(s) and a disintegrant, and
- (b) wet milling the granulated mass using a size reduction mill to produce micro granules which resist breakage during coacervation for taste-masking and whose average particle size is not more than 300 μm,
- (c) microencapsulating said microgranules with one or more polymers to provide taste-masked microcapsules with an average particle size of not more than 400 μm,
- (d) separately granulating a sugar alcohol or a saccharide or a mixture thereof having an average particle size less than 30 μm and a disintegrant to provide rapidly dispersing microgranules,
- (e) blending the taste-masked microcapsules from step (c) and rapidly dispersing microgranules from step (d) optionally with additional pharmaceutical ingredients,
- (f) compressing the blend from step (e) to form a tablet, wherein not less than 60% of the drug from said tablet dissolves in about 60 minutes when dissolution tested using USP Apparatus 2 (paddle at 50 RPM, 900 mL of 0.1N HCl at 37° C.).

15. The method of claim 14 wherein an intrabuccally rapidly disintegrating tablet is produced which comprises a sugar alcohol, a saccharide or a combination thereof, each of which have an average particle size of not more than about 30 μm, in the amount of about 30-70% by weight of the tablet, an active ingredient having an average particle diameter of not more than about 50 μm in the amount of about 0.01-30% by weight of the tablet, a disintegrant in the amount of about 1.0-10% by weight of the tablet, and optionally other pharmaceutically acceptable ingredients.

16. The method of claim 15 wherein the step of compressing includes compressing the mixture into a predetermined shape using a tablet press and pre-lubricating the dies and punches prior to tablet compression.

17. The method of claim 16 wherein the blend is internally lubricated prior to its compression on a tablet press.

18. The method of claim 15 wherein the sugar alcohol, the saccharide or the combination thereof, is selected from the group consisting of D-mannitol, sorbitol, xylitol, maltitol, and lactose and the disintegrant is selected from the group consisting of crospovidone, sodium starch glycolate, crosslinked carboxymethyl cellulose, and low substituted hydroxypropyl cellulose, each of which have an average particle diameter of not more than about 30 μm.

19. The method of claim 18 wherein the at least one drug is selected from the group consisting of $H_2$ antagonists, proton pump inhibitors, 5-$HT_1$ receptor agonists, each of which have an average particle size of not more than 50 μm, and is granulated with one or more diluents and at least one polymeric binder imparting resilient characteristics to the resulting microcapsules.

20. The method of claim 19 wherein the disintegrant is selected from the group consisting of cross-linked polyvinylpyrrolidone (crospovidone), cross-linked carmellose of sodium, low substituted hydroxypropyl cellulose and mixtures thereof.

21. The method of claim 20 wherein the tablet disintegrates within 60 seconds in the buccal cavity, the sugar is D-mannitol having an average particle size of not more than about 30 μm, the disintegrant is crospovidone, the active ingredient is ranitidine or sumatriptan having an average particle size of not more than about 50 μm and the polymeric binder is HPMC with a viscosity of 100 cps or higher, Starch 1551 or Starch 1500.

* * * * *